United States Patent
Antonelli

(10) Patent No.: US 6,890,323 B1
(45) Date of Patent: May 10, 2005

(54) SMALL VOLUME EFFUSION TRAP

(75) Inventor: Patrick Joseph Antonelli, Gainesville, FL (US)

(73) Assignee: University of Florida, Gainesville, FL (US)

( * ) Notice: Subject to any disclaimer, the term of this patent is extended or adjusted under 35 U.S.C. 154(b) by 86 days.

(21) Appl. No.: 10/309,386

(22) Filed: Dec. 3, 2002

(51) Int. Cl.[7] ............................................. A61M 1/00
(52) U.S. Cl. ..................................................... 604/319
(58) Field of Search ........................ 604/317, 319, 604/322, 326, 257; 600/573

(56) References Cited

U.S. PATENT DOCUMENTS

| | | | |
|---|---|---|---|
| 2,769,445 A * | 11/1956 | Morgavi, Jr. ................. | 604/151 |
| 3,050,062 A | 4/1962 | Ulmer | |
| 3,113,688 A * | 12/1963 | Rasmussen ............... | 73/864.03 |
| 3,610,242 A * | 10/1971 | Sheridan et al. ............. | 604/119 |
| 3,648,698 A * | 3/1972 | Doherty ....................... | 604/319 |
| 3,699,815 A | 10/1972 | Holbrook | |
| 3,742,934 A | 7/1973 | Holbrook et al. | |
| 3,774,613 A * | 11/1973 | Woods et al. ................. | 604/128 |
| 3,889,682 A * | 6/1975 | Denis et al. .................. | 604/119 |
| 4,036,231 A | 7/1977 | Dodge et al. | |
| 4,334,538 A | 6/1982 | Juhn | |
| 4,455,140 A | 6/1984 | Joslin | |
| 4,568,332 A | 2/1986 | Shippert | |
| 4,735,606 A | 4/1988 | Davison | |
| 4,813,931 A * | 3/1989 | Hauze .......................... | 604/540 |
| 5,084,034 A * | 1/1992 | Zanotti ........................ | 604/319 |
| 5,238,655 A * | 8/1993 | Laible et al. ................ | 422/101 |
| 5,312,380 A * | 5/1994 | Alchas et al. ................ | 604/319 |
| 5,363,860 A | 11/1994 | Nakas et al. | |
| 5,665,080 A | 9/1997 | Vardenberg | |
| 6,056,731 A | 5/2000 | Koetke et al. | |
| 6,207,703 B1 * | 3/2001 | Ponikau ....................... | 514/460 |

* cited by examiner

Primary Examiner—Larry I. Schwartz
Assistant Examiner—Michael G Bogart
(74) Attorney, Agent, or Firm—Saliwanchik, Lloyd & Saliwanchik

(57) ABSTRACT

A small volume effusion trap for use with common surgical or medical instruments having a housing unit with two elongate, rigid, hollow members, a vacuum source, and a drainage tube. In an embodiment, a standard, commercially available sample vial attaches to the housing unit to collect the effusion. The sample vial can be utilized directly in standardized diagnostic and/or therapeutic analysis apparatuses. To collect a small volume of effusion, one elongate, rigid, hollow member is connected to standard surgical or medical aspirators and the other elongate, rigid, hollow member is connected to the vacuum line. With suction applied to the elongate, rigid, hollow member, an area of reduced pressure is produced in the sample vial so as to cause aspirated effusion to proceed from the surgical or medical apparatus through the elongate, rigid hollow member into the sample vial.

14 Claims, 2 Drawing Sheets

SMALL VOLUME EFFUSION TRAP

FIELD OF THE INVENTION

The present invention relates to a device for gathering small volumes of effusion, and more particularly to a device that is utilized in-line with current surgical or medical apparatus and that provides ease of cleaning, re-use, and maintenance; and ease of use with research equipment to properly analyze and diagnose the issue.

BACKGROUND OF THE INVENTION

It is often difficult to drain and sample small volumes of effusion from regions in the body that are often difficult to reach including, for example, the middle ear. For example, otitis media is a middle ear infection that is extremely common and manifests itself with the presence of fluid in the middle ear. This fluid, or effusion, may be serous, mucoid, or purulent. Proper treatment often entails delicate procedures to collect and analyze a sample of the effusion. An example of such procedures is tympanocentesis, wherein needle aspiration of the middle ear is used to identify the causative organism in middle ear effusion.

The collection of bodily secretions or effusion is important for research, therapeutic analysis, and diagnosis of various diseases, infections, and other ailments. While instruments of various types have been employed in the past to collect secretion samples for therapeutic analysis and research, they do not provide ease of in-line use with current surgical or medical apparatus; ease of cleaning, re-use, and maintenance; and ease of use with research equipment to properly analyze and diagnose the issue.

In the past, tympanocentesis was performed with an Alden-Senturia trap with needle attached. Although such a trap could be utilized with surgical apparatuses, such a trap was difficult to manipulate during the procedure. Other current devices utilized in aspirating samples include U.S. Pat. No. 4,334,538 (hereinafter the '538 patent), which provides a disposable aspirator that includes a flexible tube used to reach the cavity from which the liquid specimen is to be collected. The flexible tube of the aspirator inhibits appropriate in-line use with current surgical and/or medical. Further, because the aspirators of the '538 patent are disposable, it is expensive when a great number of samples are required.

U.S. Pat. No. 5,363,860 discloses a transformable suction line. In use, the suction line is attached to an endoscope. When a sample specimen is required, the suction line can be shifted into an apparatus for trapping a specimen. The apparatus is difficult to clean and if reused repeatedly during a single operation, the samples are often contaminated.

U.S. Pat. No. 3,699,815 discloses a fluid collection container including a selectively removable insert designed to receive small amounts of bodily fluids. Because the collection container is sized to provide the reception of either small or large quantities of bodily fluids, the collection container is difficult to manipulate when performing delicate procedures to drain and obtain small volumes of effusion. Further, the device is not meant to be used in-line with surgical or medical devices.

Accordingly, there remains a need for a device that is re-usable, that can be applied to standard surgical or medical apparatus to gather small volumes of bodily fluids, and that can easily transfer the sample specimen for diagnosis and/or analysis.

BRIEF SUMMARY OF THE INVENTION

The present invention provides a device that is re-usable, that can be applied to standard surgical or medical apparatus to gather small volumes of effusion, and that can easily transfer the effusion sample for diagnosis and/or analysis. The present invention also provides a device that efficiently gathers small volumes of effusion that is easy to manipulate, clean, and maintain. Further, standard collection utilizing microcentrifuge tubes facilitate specimen processing.

According to the present invention, a device for gathering small volumes of bodily fluids includes a housing unit, a drainage tube, an inlet and an outlet opening, two elongate, rigid, hollow members, a specimen vial sized to fit diagnosis and analysis apparatuses such as micro-centrifuge tubes, a passageway from the outlet opening to the specimen vial, and a passageway from the inlet opening to the drainage tube. One elongate, rigid, hollow member connects the inlet opening to the inlet connector. The inlet connector is connectable to any surgical or medical apparatus. The other elongate, rigid, hollow member connects the outlet opening to the outlet connector. The outlet connector is connectable to a vacuum source/line.

The subject invention includes a method of use in obtaining small volume effusion from a patient. In accordance with the subject invention, the method includes the steps of (a) providing a surgical or medical apparatus and a vacuum line, (b) connecting the inlet connector to the surgical or medical apparatus, (c) connecting the outlet connector to the vacuum line, (d) attaching a sample vial over the housing unit such that both the opening to the vacuum passageway and the drainage tube are in communication with the interior of the sample vial; (e) applying negative pressure through the vacuum passageway to assist in drawing effusion from the patient into the sample vial, (e)and detaching the vial from the housing unit upon gathering a desired amount of effusion into the vial and/or detaching the device from the surgical or medical apparatus and the vacuum source/line.

DETAILED DISCLOSURE OF THE INVENTION

Figure 1:
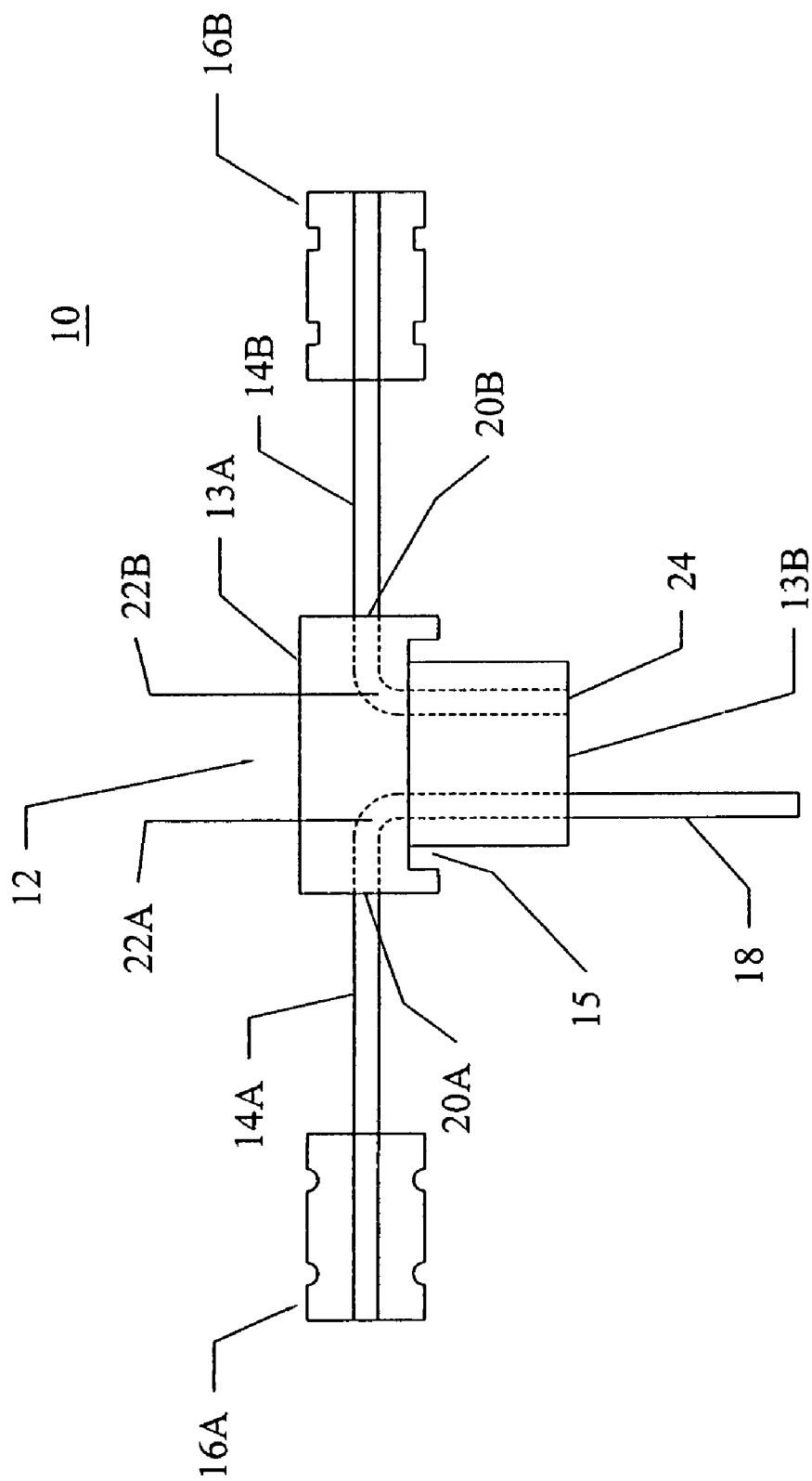
FIG. 1 illustrates a side view of the apparatus according to the present invention.

According to the present invention, a device for gathering small volumes of effusion includes a housing unit, a drainage tube, an inlet and an outlet opening, two elongate, rigid, hollow members, a sample/specimen vial sized to fit diagnosis and analysis apparatuses such as microcentrifuge tubes, a vacuum passageway from the outlet opening to the specimen vial, and an inlet passageway from the inlet opening to the drainage tube. One elongate, rigid, hollow member connects the inlet opening to the inlet connector. The inlet connector is connectable to any surgical or medical apparatus. The other elongate, rigid, hollow member connects the outlet opening to the outlet connector. The outlet connector is connectable to a vacuum source/line.

The housing unit can be sized to fit a variety of sample vials commonly used in research and analysis. For example, standard-sized microcentrifuge tubes can be applied to a device in accordance with the subject invention. Standard centrifuge tubes that can be applied to the subject invention range in size from 0.2 mL to 1,000 mL and include, but are not limited to, 0.25 mL tubes, 0.4 mL tubes, 0.6 mL tubes, and 1.5 mL tubes, 12 mL tubes, 15 mL tubes, 30 mL tubes, and 50 mL tubes.

In an embodiment, the outlet passageway from the outlet opening divides into a vacuum passageway which communicates with the interior of a specimen vial as well as to the top of the housing unit. A removable cap applied to the top of the housing unit closes the outlet passageway in communication with the top of the housing unit. In another embodiment, the inlet passageway from the inlet opening divides into a passageway to the drainage tube as well as to the top of the housing unit. A removable cap applied to the top of the housing unit closes the inlet passageway in communication with the top of the housing unit.

The inlet/outlet passageways to the top of the housing unit provide a means for controlling the suction of the subject device through the manipulation of the cap. Where the housing unit includes either an inlet or an outlet passageway to the top of the housing unit, suction is provided when the removable cap, such as a finger, bolt, or pin, is placed over the passageway in communication with the top of the housing unit. When the passageway is left uncovered, the vacuum or decrease in pressure within the sample vial is broken because the vacuum line pulls in air from the atmosphere through the passageway in communication with the top of the housing unit rather than through the more tortuous path of the sample vial.

In another embodiment where the housing unit has both an inlet and an outlet passageway to the top of the housing unit, suction is provided when the removable cap, such as a finger, bolt, or pin, is placed over both the inlet and the outlet passageways in communication with the top of the housing unit. If either passageway is left uncovered, the vacuum or decrease in pressure within the sample vial is broken because the vacuum line pulls in air from the atmosphere through the passageway in communication with the top of the housing unit rather than through the more tortuous path of the sample vial.

The inlet/outlet passageways to the top of the housing unit also provide a means for cleaning the subject device through the manipulation of the cap. The inlet/outlet passageways to the top of the housing unit permit ease of cleaning the housing unit. For example, by using such conventional methods as inserting a wire or wire brush into inlet/outlet passageways in communication with the top of the housing unit, the ordinary skilled artisan can remove any debris in the inlet/outlet passageways.

The subject invention includes a method of use in obtaining small volume effusion from a patient. In accordance with the subject invention, the method includes the steps of (a) providing a surgical or medical apparatus and a vacuum line, (b) connecting the inlet connector opening to the surgical or medical apparatus, (c) connecting the outlet connector opening to the vacuum line, (d) attaching a sample vial over the housing unit so that the interior of the sample vial incorporates both the drainage tube and the opening to the vacuum passageway, (e) applying a vacuum to the vacuum passageway opening to the sample vial to draw effusion into the vial, (f) detaching the vial from the housing unit upon gathering a desired amount of effusion into the vial. In a related embodiment, the method further includes the step of (g) detaching the device according to the present invention from the surgical or medical apparatus and the vacuum line, once the procedure for obtaining patient effusion is complete.

As illustrated in FIG. 1, the small volume effusion trap device 10 includes a housing unit 12, two elongate, rigid, hollow members 14a, 14b; an inlet connector 16a and an outlet connector 16b; and a drainage tube 18.

The housing unit 12 can be formed from a variety of materials and shapes. The lower portion of 13b of the housing unit 12 is shaped to fit a sample vial and to provide a substantially airtight connection between a surface of the housing unit and an open end of a detachable, sample vial (not shown). For example, current sample vials include a neck at an open end and a projecting collar to permit insertion of the vial into a corresponding cavity 15 in the upper portion 13a of the housing unit 12 to produce a connection that is substantially airtight. The upper portion 13a of the housing unit 12 also includes an inlet opening 20a and an outlet opening 20b. The housing unit 12 further includes an inlet passageway 22a that travels from the inlet opening 20a through the upper portion 13a of the housing unit 12 down into the lower portion 13b of the housing unit 12 to the drainage tube 18. The housing unit 12 also includes a vacuum passageway 22b from the outlet opening 20b that travels through the upper portion 13a of the housing unit 12 down into the lower portion 13b of the housing unit 12 to a vacuum opening 24. The drainage tube 18 and the vacuum opening 24 are located on the bottom portion 13b of the housing unit 12 such that the opening of the sample vial would encompass the drainage tube 18 and the vacuum opening 24.

An elongate, rigid, hollow member 14a connects the inlet opening 20a to the inlet connector 16a. Another elongate, rigid, hollow member 14b connects the outlet opening 20b to the outlet connector 16b. The inlet connector 16a is connectable to any surgical or medical apparatus used to draw small volume effusions from a patient. The outlet connector 16b is connectable to a vacuum source/line. When the vacuum source/line is in operation, negative pressure is created to assist in drawing effusion from a patient into the sample vial.

Specifically, the passageways 22a, 22b of the housing unit 12 are fashioned so that upon application of a vacuum source/line to the elongate, rigid, hollow member 14b, an area of reduced pressure is presented inside the sample vial so as to cause the aspirated effusion to proceed through the elongate, rigid, hollow member 14a into the inlet passageway 22a and the drainage tube 24 to finally deposit in the interior of the sample vial.

In a preferred embodiment, the inlet connector 16a and the outlet connector 16b both measure roughly 0.5 inches in length and roughly 0.3 inches in diameter. Elongate, rigid, hollow members 14a, 14b can be of any length including, for example, roughly 0.9 inches in length from the housing unit 12 through the inlet connector 16a or the outlet connector 16b. The elongate, rigid members 14a, 14b each have a hollow interior that measures roughly 0.06 inches in diameter. The upper portion 13a of the housing unit 12 measures roughly 0.5 inches in diameter. The inlet passageway 22a and outlet passageway 22b measure roughly 0.8 inches in diameter. The drainage tube 24 measures roughly 0.5 inches in length and includes a hollow interior of sufficient diameter to allow drainage of effusion into a sample vial.

Figure 2:
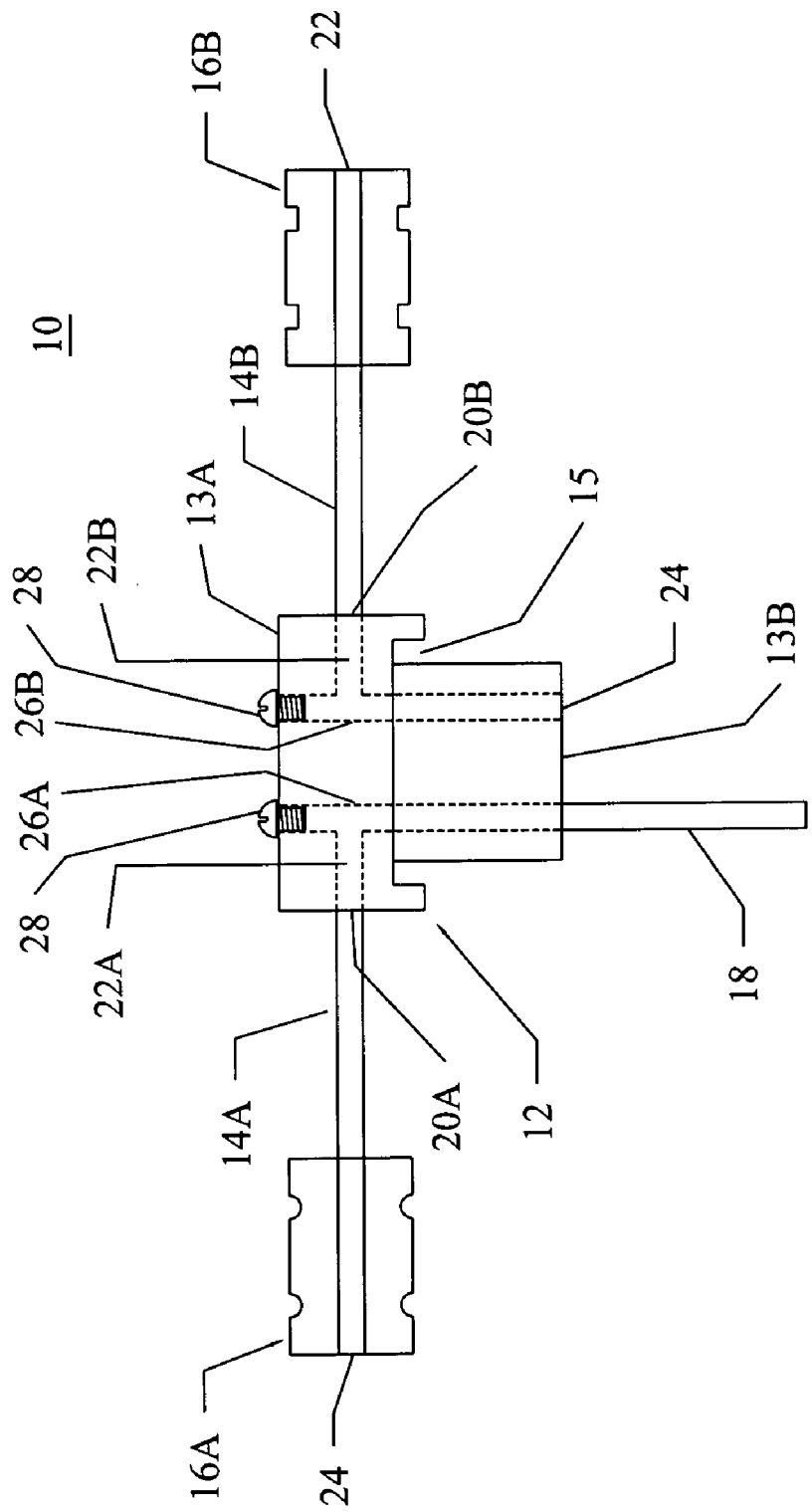
FIG. 2 illustrates a side view of an embodiment according to the present invention.

In FIG. 2, an embodiment with inlet/outlet passageways to the top of the housing unit is represented. The outlet passageway 22b from the outlet opening 20b divides into a vacuum passageway which communicates with the interior of a specimen vial at the vacuum opening 24 and into an outlet/housing unit passageway 26b that communicates with the top of the housing unit 12. A removable cap can be applied at the top of the housing unit 12 into the opening to the outlet/housing unit passageway 26b to close the outlet/ housing unit passageway 26b and prevent communication between the outlet/housing unit passageway 26b and ambient air. In another embodiment, the inlet passageway 22a from the inlet opening 20a divides into a passageway to the drainage tube 18 and into an inlet/housing unit passageway 26a that communicates with the top of the housing unit 12. A removable cap can be applied to the top of the housing unit 12 into the inlet/housing unit passageway 26a to prevent communication between the inlet/housing unit passageway 26a with the ambient air. The removable cap includes any object that can prevent communication between the inlet or outlet/housing unit passageways 26a, 26b from communicating with the ambient air. As illustrated in FIG. 2, the removable cap can include a bolt 28.

The inlet/outlet passageways 26a, 26b to the top of the housing unit 12 provide a means for controlling the suction of the subject device through the manipulation of the cap. Where the housing unit 12 includes either an inlet/housing unit passageway 26a or an outlet/housing unit passageway 26b to the top of the housing unit, negative pressure is provided when the removable cap, such as a bolt 28, finger, bolt, or pin, is placed over the opening to either the inlet/outlet housing unit passageway 26a, 26b. When the inlet/outlet housing unit passageway 26a, 26b is open to ambient air, the vacuum or decrease in pressure within the sample vial is broken because the vacuum source/line pulls in air from the atmosphere through the passageway in communication with the top of the housing unit 12 rather than through the more tortuous path of the sample vial. Where the housing unit 12 has both an inlet/housing unit passageway 26a and an outlet/housing unit passageway 26b to the top of the housing unit 12, negative pressure is provided when the removable cap, such as a bolt 28, finger, bolt, or pin, is placed over the opening at the top of the housing unit 12 to the inlet/housing unit passageway 26a and the opening at the top of the housing unit 12 to the outlet/housing unit passageway 26b. If either opening to passageway 26a, 26b is left uncovered, the vacuum or decrease in pressure within the sample vial is broken because the vacuum source/line pulls in air from the atmosphere through the passageway in communication with the top of the housing unit rather than through the more tortuous path of the sample vial.

The inlet/outlet housing unit passageways 26a, 26b to the top of the housing unit 12 also provide a means for cleaning the device 10 through the manipulation of the cap. The inlet/outlet housing unit passageways 26a, 26b to the top of the housing unit pennit ease of cleaning the housing unit 12. For example, by using such conventional methods as inserting a wire or wire brush into inlet/outlet housing unit passageways, the ordinary skilled artisan can easily remove any debris in the inlet/outlet passageways.

The sample vial used according to the present invention is one that can be commercially procured and readily applied to conventional analysis and diagnostic equipment. Examples of suitable sample vials include micro-centrifuge tubes that can readily be applied to micro-centrifuge equipment.

The subject invention includes a method in obtaining small volume effusion from a patient. In accordance with the subject invention, the method includes the steps of (a) providing a surgical or medical apparatus and a vacuum source/line, (b) connecting the inlet opening to the surgical or medical apparatus, (c) connecting the outlet opening to the vacuum source/line, (d) attaching a sample vial over the housing unit to apply a vacuum to the passageway from the outlet opening to the sample vial to draw effusion into the vial, (e) detaching the vial from the housing unit upon gathering a desired amount of effusion into the vial, and (f) detaching the device from the surgical or medical apparatus and the vacuum line to cease operation of the subject invention.

In an alternate embodiment, the housing unit includes an inlet/housing unit passageway 26a or an outlet/housing unit passageway 26b to the top of the housing unit 12. A method of use for this embodiment includes the steps of (a) providing a surgical or medical apparatus and a vacuum source/line, (b) connecting the inlet opening to the surgical or medical apparatus, (c) connecting the outlet opening to the vacuum source/line, (d) attaching a sample vial over the housing unit such that both the drainage tube and the opening to the vacuum passageway are located in the interior of the sample vial; (e) closing the inlet/housing unit passageway 26a or the outlet/housing unit passageway 26b to provide negative pressure within the sample vial to draw effusion into the vial, (f) collecting the desired amount of effusion within the vial, (g) opening the inlet/housing unit passageway 26a or the outlet/housing unit passageway 26b to break the vacuum created within the sample vial, (h) detaching the vial from the housing unit, (i) detaching the device from the surgical or medical apparatus, and (j) detaching the device from the vacuum source/line to cease operation of the subject invention.

In a related embodiment, an inlet/housing unit passageway 26a is included in combination with the outlet/housing unit passageway 26b within the housing unit 12. The method of use for this embodiment is similar to the method described above, including the steps of (a) providing a surgical or medical apparatus and a vacuum source/line, (b) connecting the inlet opening to the surgical or medical apparatus, (c) connecting the outlet opening to the vacuum source/line, (d) attaching a sample vial over the housing unit such that both the drainage tube and the opening to the vacuum passageway are located in the interior of the sample vial;(e) closing both the inlet and the outlet/housing unit passageways 26a, 26b to provide negative pressure within the sample vial to draw effusion into the vial, (f) collecting the desired amount of effusion within the vial, (g) opening either/both the inlet and/or the outlet/housing unit passageways 26a, 26b to break the vacuum created within the sample vial, (h) detaching the vial from the housing unit, (i) detaching the device from the surgical or medical apparatus, and (j) detaching the device from the vacuum source/line to cease operation of the subject invention.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A re-usable small volume effusion trap comprising:
   a. a housing unit comprising an upper portion, a bottom portion, an inlet opening, an outlet opening, an inlet passageway that connects the inlet opening to a drainage tube, and a vacuum passageway that connects the outlet opening to a vacuum opening; wherein the drainage tube and the vacuum opening are located on the bottom portion of the housing unit; wherein the inlet passageway and the vacuum passageway also communicate with a top-facing surface of the housing unit; wherein the inlet opening and the outlet opening are not located on the top-facing surface of the housing unit; wherein the upper portion of the housing unit is shaped to fit an opening of a detachable, standard-sized sample vial;
b. at least two elongate, rigid, hollow members;
c. an inlet connector; and
d. an outlet connector;

wherein a first elongate, rigid hollow member connects the inlet opening to the inlet connector, and wherein a second elongate, rigid hollow member connects the outlet opening to the outlet connector.

2. The effusion trap according to claim 1, wherein the inlet passageway and the vacuum passageway measure about 0.8 inches in diameter, wherein the inlet connector measures about 0.5 inches in length and about 0.3 inches in diameter, and wherein the elongate, rigid, hollow members are about 0.9 inches in length from the housing unit through the inlet connector or the outlet connector and the hollow interior measures about 0.06 inches in diameter.

3. The effusion trap according to claim 1, further comprising at least one removable cap.

4. The effusion trap according to claim 1, wherein the sample vial is a microcentrifuge tube.

5. The effusion trap according to claim 4, wherein the microcentrifuge tube is a 1.5 mL tube.

6. The effusion trap according to claim 1, wherein the drainage tube measures about 0.5 inches in length and includes a hollow interior of sufficient diameter to allow drainage of effusion into the sample vial.

7. A method for obtaining small volume effusion from a patient comprising:
a. providing a surgical or medical apparatus and a vacuum line;
b. providing a re-usable small volume effusion trap comprising a housing unit comprising an upper portion, a bottom portion, an inlet opening; an outlet opening; an inlet passageway and a vacuum passageway; at least two elongate, rigid, hollow members; an inlet connector; an outlet connector; a vacuum opening; and a drainage tube, wherein the upper portion of the housing unit is shaped to fit an opening of a detachable, sample vial, wherein the inlet passageway connects the inlet opening to the drainage tube; and wherein the vacuum passageway connects the outlet opening to the vacuum opening, wherein the inlet passageway and the vacuum passageway also communicate with a top facing surface of the housing unit; wherein the inlet opening and the outlet opening are not located on the top-facing surface of the housing unit;
c. connecting the inlet connector to the surgical or medical apparatus;
d. connecting the outlet connector to the vacuum line;
e. attaching the sample vial to the housing unit so that the interior of the sample vial incorporates both the drainage tube and the opening to the vacuum passageway;
f. applying a vacuum to the vacuum passageway to the sample vial to draw effusion into the vial; and
g. detaching the vial from the housing unit upon gathering a desired amount of effusion into the vial.

8. The method according to claim 7, further comprising the step of detaching the effusion trap from the surgical or medical apparatus and the vacuum line, once the procedure for obtaining patient effusion is complete.

9. The method according to claim 7, wherein the inlet passageway and the vacuum passageway measure about 0.8 inches in diameter, wherein the inlet connector measures about 0.5 inches in length and about 0.3 inches in diameter, and wherein the elongate, rigid, hollow members are about 0.9 inches in length from the housing unit through the inlet connector or the outlet connector and the hollow interior measures about 0.06 inches in diameter.

10. The method according to claim 7, further comprising the steps of covering the inlet passageway and covering the vacuum passageway at the top of the housing unit to create a vacuum within the sample vial.

11. The method according to claim 7, wherein the effusion trap further comprises at least one removable cap.

12. The method according to claim 11, further comprising the step of removing the removable cap to break the vacuum created within the sample vial.

13. The method according to claim 7, wherein the sample vial is a microcentrifuge tube.

14. The method according to claim 13, wherein the microcentrifuge tube is 1.5 mL tube.

* * * * *